US012788230B2

(12) United States Patent
Fan et al.

(10) Patent No.: US 12,788,230 B2
(45) Date of Patent: Nov. 10, 2026

(54) CABLE ANCHORING DEVICE FOR ENDOSCOPE

(71) Applicant: Medimaging Integrated Solution, Inc., Hsinchu (TW)

(72) Inventors: Yueh-Ying Fan, Hsinchu Science Park (TW); Chia-Jung Lee, Hsinchu Science Park (TW)

(73) Assignee: Medimaging Integrated Solution, Inc., Hsinchu (TW)

( * ) Notice: Subject to any disclaimer, the term of this patent is extended or adjusted under 35 U.S.C. 154(b) by 217 days.

(21) Appl. No.: 18/661,258

(22) Filed: May 10, 2024

(65) Prior Publication Data

US 2025/0228440 A1 Jul. 17, 2025

(30) Foreign Application Priority Data

Jan. 12, 2024 (TW) ................................ 113200478

(51) Int. Cl.
*A61B 1/005* (2006.01)
*A61B 1/00* (2006.01)

(52) U.S. Cl.
CPC ........ *A61B 1/0057* (2013.01); *A61B 1/00128* (2013.01)

(58) Field of Classification Search
CPC .......................... A61B 1/0057; A61B 1/00128
See application file for complete search history.

(56) References Cited

U.S. PATENT DOCUMENTS

| | | | | |
|---|---|---|---|---|
| 5,372,587 A * | 12/1994 | Hammerslag | A61M 25/0144 604/95.04 |
| 11,382,497 B2 * | 7/2022 | Ide | A61B 1/0057 |
| 11,612,304 B2 * | 3/2023 | Viebach | A61B 1/00091 600/109 |
| 11,931,001 B2 * | 3/2024 | Do | A61B 1/0011 |
| 12,133,627 B2 * | 11/2024 | Harada | A61B 1/122 |
| 12,220,106 B2 * | 2/2025 | Lee | A61B 1/00006 |
| 2009/0227842 A1 * | 9/2009 | Ando | A61B 1/0055 600/146 |
| 2011/0245808 A1 * | 10/2011 | Voeller | A61M 25/0054 604/528 |
| 2012/0035617 A1 * | 2/2012 | Joshi | A61B 17/0218 606/130 |

(Continued)

*Primary Examiner* — Anhtuan T Nguyen
*Assistant Examiner* — Shankar Raj Ghimire
(74) *Attorney, Agent, or Firm* — MUNCY, GEISSLER, OLDS & LOWE, P.C.

(57) ABSTRACT

A steering joint wire rope fixing device is provided. The steering joint wire rope fixing device includes a front-end assembly, a cable and a resin. The front-end assembly includes a channel part and a groove. The channel part is located between two ends of the front-end assembly. The groove is located between one end of the front-end assembly and the channel part, and the channel part and the groove are interconnected. A part of the cable passes through the channel part and the groove. The resin is placed in the groove to fix the part of the cable located in the groove. Therefore, the invention can fix the steel cable in a limited space and reduce the overall volume. Further, the invention can prevent the cable cuts from protruding or the workpieces from falling off. Besides, the invention can decrease assembly time and reduce cost of parts and fabrication.

10 Claims, 12 Drawing Sheets

1B

1A

(56) References Cited

U.S. PATENT DOCUMENTS

| | | | | |
|---|---|---|---|---|
| 2012/0289938 | A1* | 11/2012 | Northrop | A61M 25/09 604/528 |
| 2015/0065807 | A1* | 3/2015 | Greenberg | A61B 1/05 600/207 |
| 2017/0035274 | A1* | 2/2017 | Mikkaichi | A61B 1/00 |
| 2018/0035869 | A1* | 2/2018 | Yamaya | A61B 1/00098 |
| 2019/0254504 | A1* | 8/2019 | Ide | A61B 1/018 |
| 2020/0187765 | A1* | 6/2020 | Ide | G02B 23/2469 |
| 2020/0237185 | A1* | 7/2020 | Do | A61M 25/0147 |
| 2020/0237189 | A1* | 7/2020 | Do | A61B 1/0011 |
| 2021/0361144 | A1* | 11/2021 | Hatano | A61B 1/0008 |
| 2021/0378648 | A1* | 12/2021 | Thissen | A61B 17/00234 |
| 2023/0122213 | A1* | 4/2023 | Harada | A61B 8/0841 600/471 |
| 2023/0233062 | A1* | 7/2023 | Harada | A61B 1/00098 600/107 |
| 2023/0248225 | A1* | 8/2023 | Suwa | A61B 1/00098 600/137 |
| 2023/0380674 | A1* | 11/2023 | Harada | A61B 1/00098 |
| 2024/0122458 | A1* | 4/2024 | Fuchs | A61B 1/0055 |
| 2025/0098945 | A1* | 3/2025 | Hansen | A61B 1/0011 |
| 2025/0151991 | A1* | 5/2025 | Marrion | A61B 1/0011 |
| 2025/0302282 | A1* | 10/2025 | Harada | A61B 1/00137 |

* cited by examiner

CABLE ANCHORING DEVICE FOR ENDOSCOPE

BACKGROUND OF THE INVENTION

1. Field of the Invention

The present invention relates to an endoscope technology, particularly to a cable anchoring device for an endoscope.

2. Description of the Prior Art

The camera of an endoscope is normally steered via operating a steering joint and the wire ropes thereof. There are two methods to fix wire ropes to a steering joint. The first one is winding the wire rope around a knob inside the steering joint. The current trend is to miniaturize the endoscope. Therefore, the interior space thereof is very limited. Winding a wire rope thereinside may risk protrusion of the knot of the wire rope, raising assembly difficulty, impairing fabrication automation, and impeding structure miniaturization. The second method is joining a block structure (such as a metal block), whose size is larger than the hole for the wire rope, to the steering joint for anchoring the wire rope in steering the camera. However, the metal block, which is joined to the steering joint afterward, may risk dropping.

Accordingly, the present invention proposes a cable anchoring device for an endoscope, which favors reducing overall volume and exempts wire ropes from dropping, to overcome the conventional problems.

SUMMARY OF THE INVENTION

One objective of the present invention is to provide a cable anchoring device for an endoscope, which allows the wire rope to be fixed in a limited space, prevents the cuts of the wire ropes and the workpieces from protruding or dropping, decreases assembly time, and reduces the costs of parts and fabrication.

According to the abovementioned objective, the present invention proposes a cable anchoring device for an endoscope, which comprises a front-end assembly, a cable and a resin. The front-end assembly includes a channel part and a groove. The channel part is arranged between two ends of the front-end assembly. The groove is arranged between one end of the front-end assembly and the channel part. The channel part interconnects with the groove. A portion of cable is inserted into the channel part and the groove. The resin is dispensed into the groove to fix the portion of cable inside the groove.

In one embodiment, the groove has a lateral face and a guiding face opposite to the lateral face. The lateral face neighbors the channel part. The guiding face is extended upward from the bottom of the groove and gradually tilts until it reaches a surface of the front-end assembly.

In one embodiment, the channel part further includes a first channel and a second channel. One end of the first channel has a first via-hole, and another end of the first channel has a second via-hole. One end of the second channel has a third channel, and another end of the second channel has a fourth via-hole. The cable may be inserted into the first via-hole to pass through the first channel and then protrude from the second via-hole to reach the groove. Then, the cable is inserted into the fourth via-hole to enter the second channel.

In one embodiment, one end of the cable has a cephalization structure inside the groove. The size of the cephalization structure is larger than the diameter of the opening of the channel part.

In one embodiment, the channel part further includes a first channel and a trench. The first channel is arranged between two ends of the front-end assembly. One end of the first channel has a first via-hole, and another end of the first channel has a second via-hole. The trench is a recessed portion arranged in a region where a surface of the front-end assembly interconnects with the groove. One end of the cable may pass through the first via-hole, the first channel, the second via-hole and the groove in sequence and then enters the trench. A first protrusion is established on one side of the trench, and a second protrusion is established on another side of the trench, wherein the first protrusion and the second protrusion are arranged in a staggering way. The first protrusion and the second protrusion are used to confine the cable inside the trench.

In one embodiment, the front-end assembly further includes an outer-rim trench; the outer-rim trench is extended along an outer diameter of the front-end assembly and interconnected with the groove. Another portion of the cable is received by the outer-rim trench and the groove. A third protrusion and a fourth protrusion are formed in the outer-rim trench. The third protrusion and the fourth protrusion are respectively disposed on two sides of the outer-rim trench and arranged in a staggering way. The cable is confined inside the outer-rim trench.

Therefore, the present invention may be applied to the front end of an endoscope to steer the optical image sensing module of the endoscope. The present invention overcomes the conventional problems, realizing fast assembly and reducing the cost of parts. Further, the present invention exempts the personnel from being harmed by the protruding cuts of wire ropes and promotes safety. Furthermore, the present invention favors miniaturization of endoscopes.

The objective, technologies, features and advantages of the present invention will become apparent from the following description in conjunction with the accompanying drawings wherein certain embodiments of the present invention are set forth by way of illustration and example.

BRIEF DESCRIPTION OF THE DRAWINGS

The foregoing conceptions and their accompanying advantages of this invention will become more readily appreciated after being better understood by referring to the following detailed description, in conjunction with the accompanying drawings, wherein.

DESCRIPTION OF THE PREFERRED EMBODIMENTS

Figure 1:
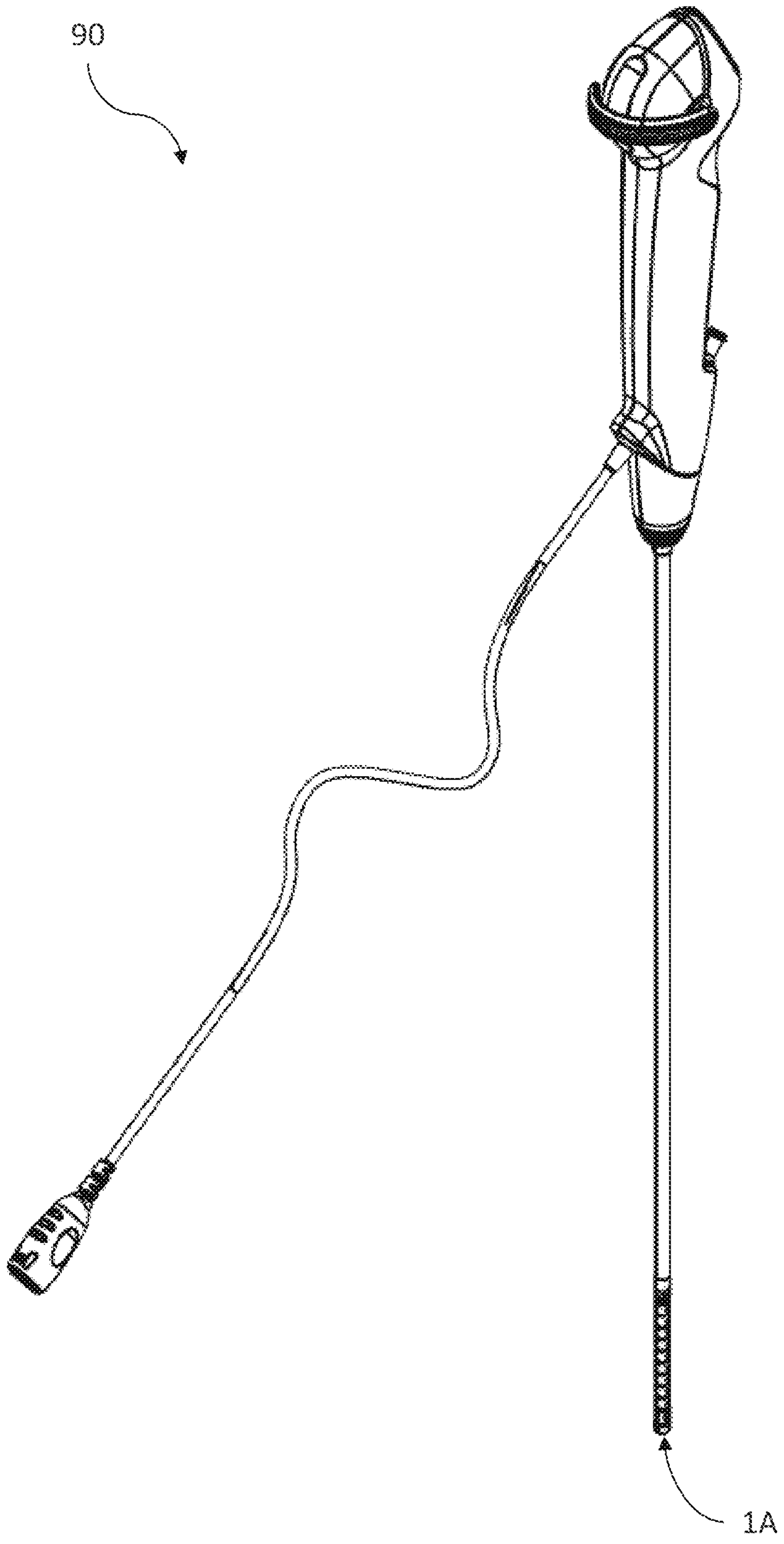
FIG. 1 is a diagram schematically showing that a cable anchoring device for an endoscope is applied to an endoscope according to one embodiment of the present invention.
Figure 2:
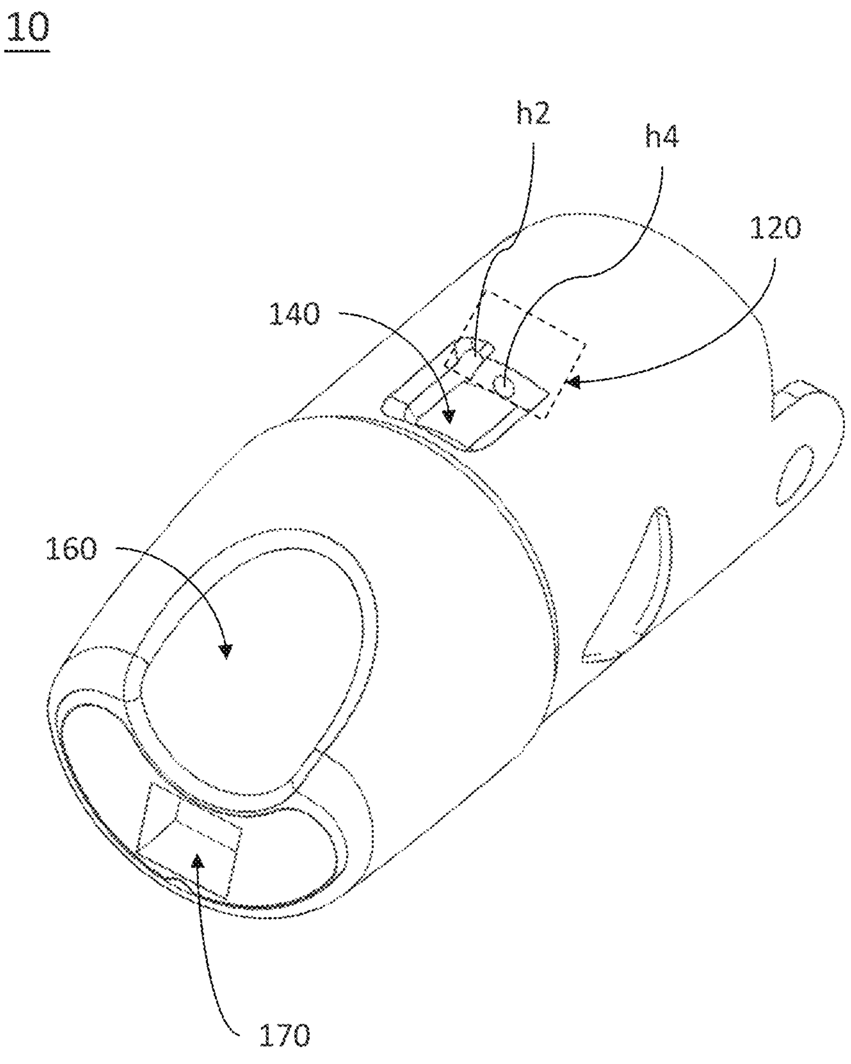
FIG. 2 is a diagram schematically showing a front-end assembly of a cable anchoring device for an endoscope according to a first embodiment of the present invention.

The embodiments of the present invention will be further demonstrated in details hereinafter in cooperation with the corresponding drawings. In the drawings and the specification, the same numerals represent the same or the like elements as much as possible. For simplicity and convenient labelling, the shapes and thicknesses of the elements may be exaggerated in the drawings. It is easily understood: the elements belonging to the conventional technologies and well known by the persons skilled in the art may be not particularly depicted in the drawings or described in the specification. Various modifications and variations made by the persons skilled in the art according to the contents of the present invention are to be included by the scope of the present invention.

Figure 3:
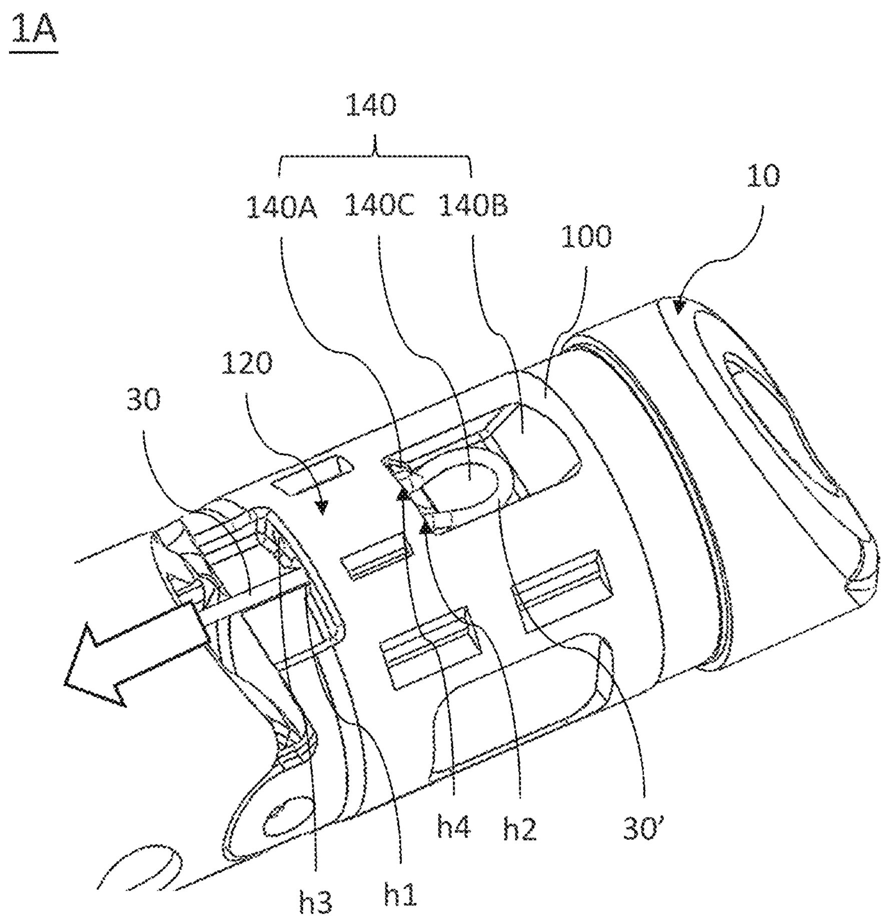
FIG. 3 is a diagram schematically showing the cable anchoring device for an endoscope according to the first embodiment of the present invention.
Figure 4:
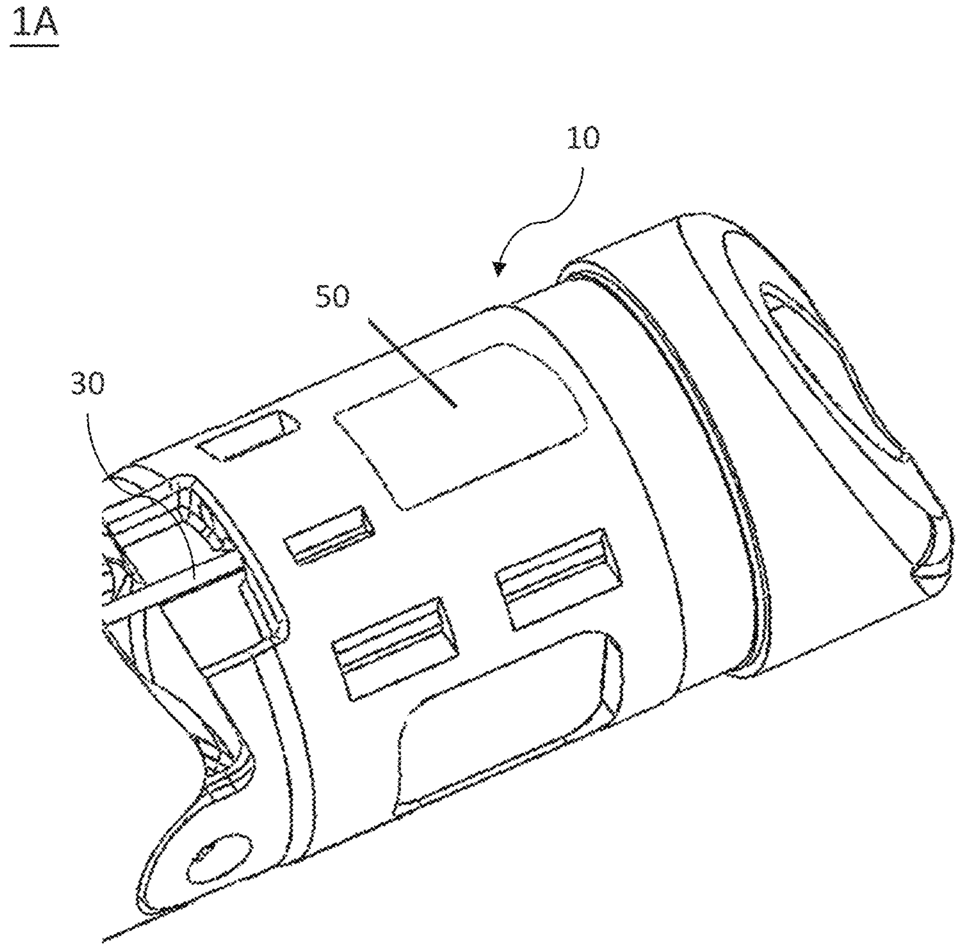
FIG. 4 is a diagram schematically showing a resin of the cable anchoring device for endoscope according to the first embodiment of the present invention.

FIGS. 1-6 are diagrams schematically showing a cable anchoring device for an endoscope 1A according to a first embodiment of the present invention. Refer to FIG. 1. The cable anchoring device for an endoscope 1A is applicable to an endoscope 90, disposed at a front end of the endoscope 90 and used to steer an optical image sensing module at the front of the endoscope 90. Refer to FIGS. 2-6. The cable anchoring device for endoscope 1A comprises a front-end assembly 10, a cable 30, and a resin 50. The front-end assembly 10 includes a channel part 120 and a groove 140. The channel part 120 is located between two ends of the front-end assembly 10. The groove 140 is located between one end of the front-end assembly 10 and the channel part 120; the channel part 120 is interconnected with the groove 140. The front-end assembly 10 may be but is not limited to be fabricated in an injection technology or a molding technology. The front-end assembly 10 may further include a working channel 160 and an accommodation space 170 of an image sensing-illumination module. The working channel 160 occupies a larger space for receiving surgical instruments thereinside. One end of the working channel 160 neighbors the accommodation space 170 of the image sensing illumination module. A part of the cable 30 is inserted into the channel part 120 and the groove 140. The cable 30 may be but is not limited to be a steel wire rope, which features corrosion resistance, rust resistance, fatigue resistance and flexibility. Considering the quality of the cable 30, the steel wire rope is a suitable material because it is stable in quality. Therefore, a steel wire rope is normally adopted as the cable 30. However, the present invention does not restrict that the cable 30 must be a steel wire rope. The resin 50 is disposed in the groove 140 for fixing the part of cable 30 inside the groove 140. As shown in FIG. 3, the part of cable 30 inside the groove 140 is termed as a loop 30' thereinafter. In this embodiment or other embodiments, two groups of the channel parts 120 and the grooves 140 may be symmetrically arranged on two sides of the front-end assembly 10, and two cables 30 may be respectively disposed on two sides of the front-end assembly 10. Although the drawings only show the channel part 120, the groove 140 and the cable 30 of a single side, the persons having ordinary knowledge in the art should know that the channel parts 120, the grooves 140 and the cables 30 may be disposed on two sides of the front-end assembly 10 to control the direction of the front-end assembly 10.

The groove 140 is a space for dispensing resin to fix the cable, having a lateral face 140A and a guiding face 140B opposite to the lateral face 140A. The lateral face 140A neighbors the channel part 120. The guiding face 140B starts from the bottom 140C of the groove 140 and gradually tilts until it reaches a surface 100 of the front-end assembly 10. It should be noted: the inclined plane of the guiding face 140B may guide the cable 30 to protrude from the groove 140 and provides sufficient space for the subsequent operations. In the fabrication process, the cable 30 is pulled back to decrease the size of the loop 30' to completely sink the loop 30' inside the groove 140. Next, the resin 50 is dispensed into the groove 140. Then, the loop 30' is securely fixed by the resin dispensing method to prevent the cable 30 from displacement.

Figure 5:
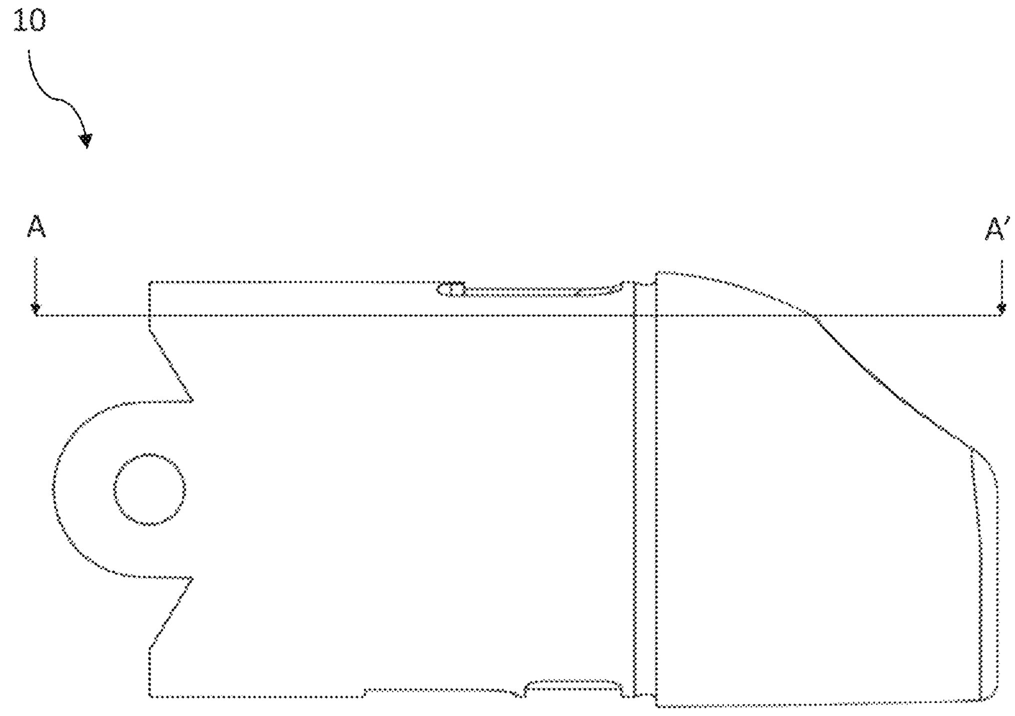
FIG. 5 is a side view schematically showing the front-end assembly of the cable anchoring device for an endoscope according to the first embodiment of the present invention.
Figure 6:
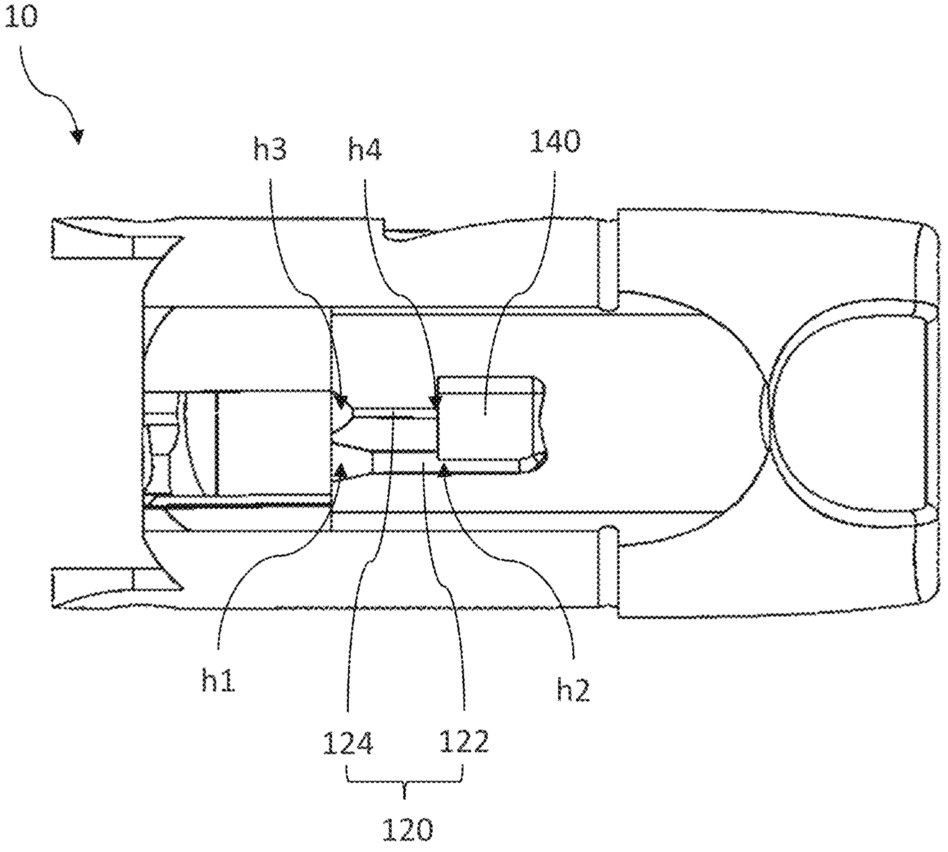
FIG. 6 is a sectional view along Line A-A' of the front-end assembly in FIG. 5.

Refer to FIG. 5 and FIG. 6. FIG. 6 shows a sectional view to clearly illustrate the structure of the channel part 120. The channel part 120 further includes a first channel 122 and a second channel 124. One end of the first channel 122 has a first via-hole h1, and another end of the first channel 122 has a second via-hole h2. One end of the second channel 124 has a third channel h3, and another end of the second channel 124 has a fourth via-hole h4. The cable 30 may be inserted into the first via-hole h1 to pass through the first channel 122 and then protrude from the second via-hole h2 to reach the groove 140. Then, the cable 30 is inserted into the fourth via-hole h4 to enter the second channel 124. After being inserted into the second channel 124, one end of the cable 30 does not protrude from the third via-hole h3 but is flush-cut with respect to the surface where the third via-hole h3 appears. Thereby, the head end of the cable does not protrude from the surface of the camera assembly. Further, the friction generated between the bent cable and the structure may function to counteract the pulling force. Besides, the structure between the first channel 122 and the second channel 124 can provide sufficient support force.

It is easily understood: in order to facilitate inserting the cable 30 in a narrow space, the first via-hole h1, the second via-hole h2, the third via-hole h3 or the fourth via-hole h4 is preferably but is not limited to be a trumpet-shape opening-expanded hole. Alternatively, some of the first via-hole h1, the second via-hole h2, the third via-hole h3 and the fourth via-hole h4 are trumpet-shape opening-expanded holes. Via the guiding structure having a trumpet-shape opening-expanded hole, the cable 30 is inserted through the first channel 122 and runs along the first channel 122 to contact the guiding face 140B. The slope of the guiding face 140B lifts up the cable 30. Then, the cable 30 is inserted into the fourth via-hole h4. Thereby, the cable 30 is easy to insert and regulate. Thus, the cable 30 can be tightened up, and the resin is dispensed to fix the cable 30.

Figure 7A:
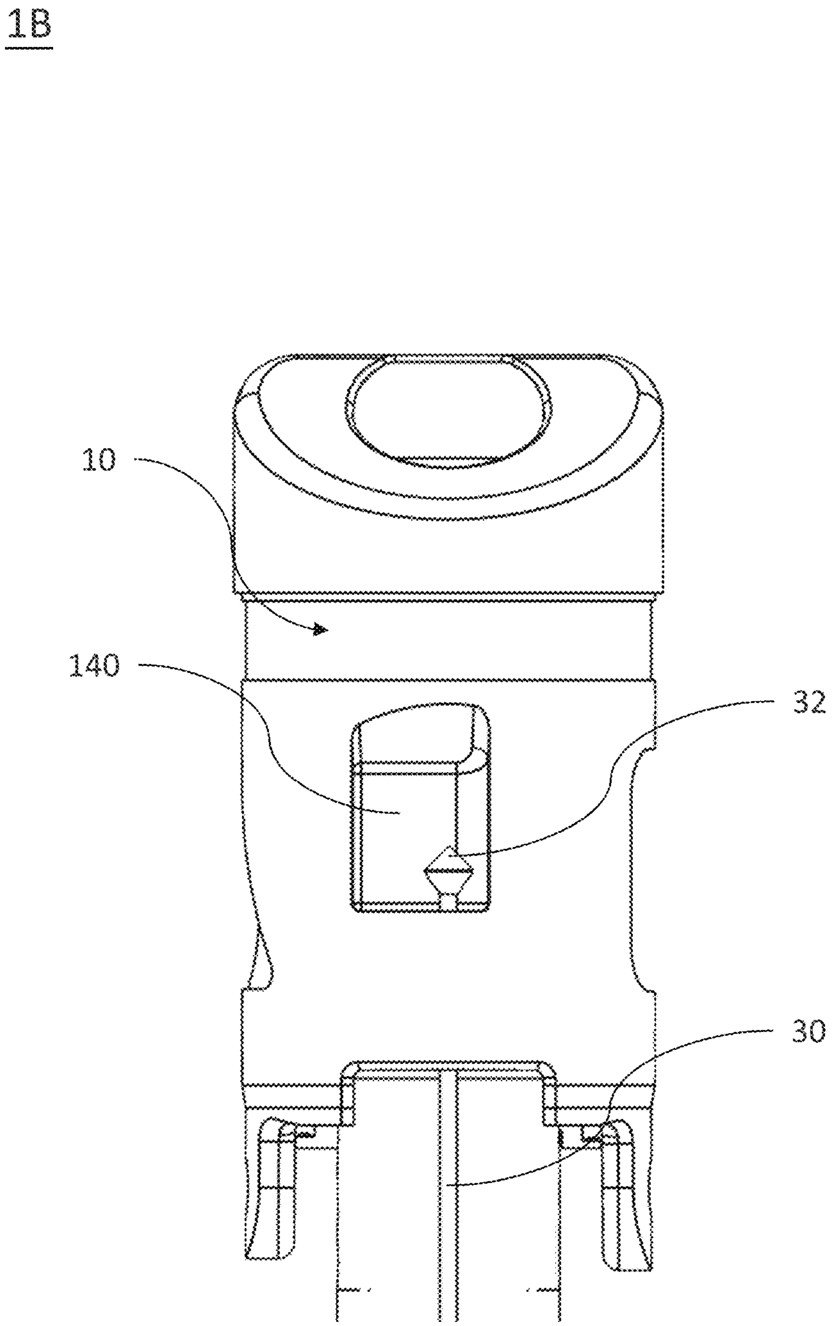
FIG. 7A is a diagram schematically showing a cable anchoring device for an endoscope according to a second embodiment of the present invention.
Figure 7B:
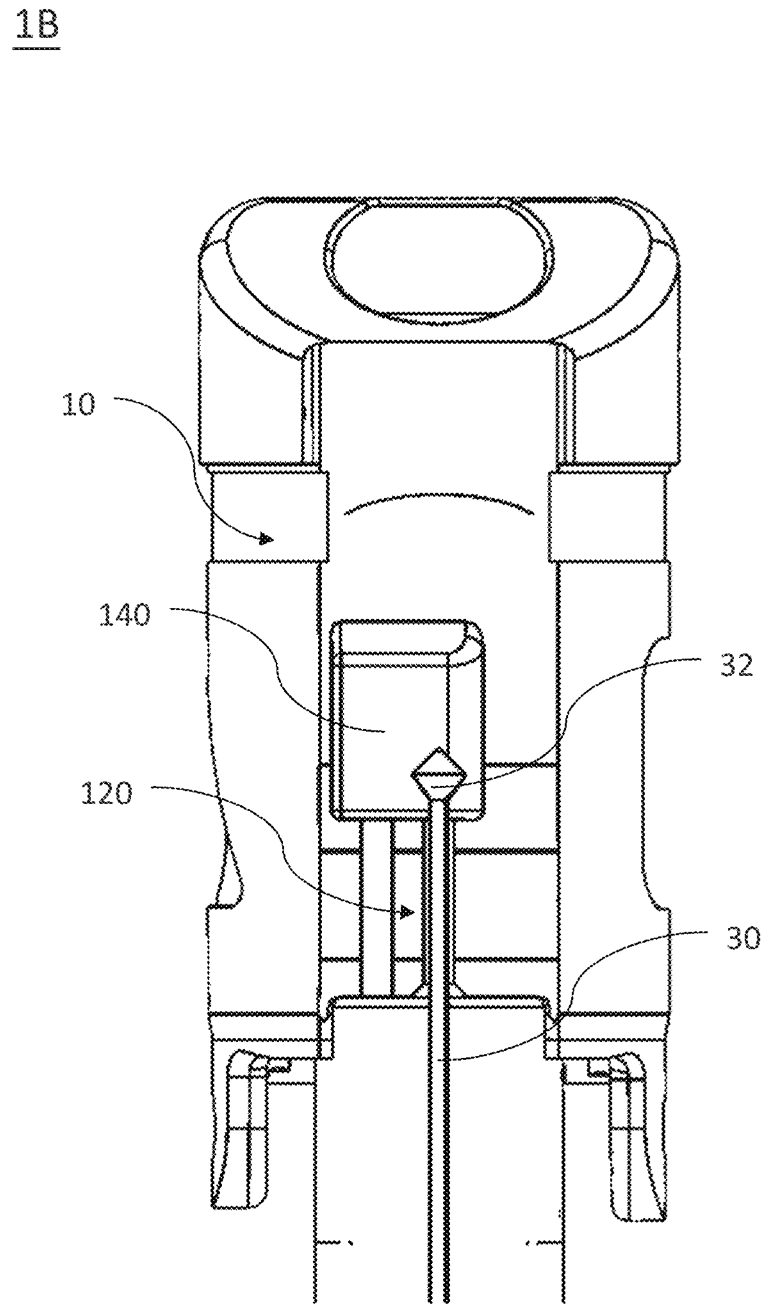
FIG. 7B is a sectional view of the cable anchoring device for an endoscope in FIG. 7A.

Below is introduced a second embodiment of the present invention. Refer to FIG. 7A and FIG. 7B. The cable anchoring device for an endoscope 1B of the second embodiment is different from that of the first embodiment is in the shape and structure of one end of the cable 30. In the second embodiment, one end of the cable 30 has a cephalization structure 32 inside the groove 140. The size of the cephalization structure 32 is larger than the diameter of the opening of the channel part 120. To say it more exactly, the size of the cephalization structure 32 is larger than the diameter of the second via-hole h2. The shape of the cephalization structure 32 may be but is not limited to be a ball, an ellipse, a cone, a rhombus, or a hemisphere. The cable 30 may be but is not limited to be a steel wire rope. The fabrication method of the cephalization structure 32 may be but is not limited to be a laser technology or a welding technology, wherein one end of the cable 30 may be melted to form the cephalization structure 32 by a laser fusion device or a welding machine. Via forming the cephalization structure 32, one end of the cable 30 will be larger than the second via-hole h2. Thereby, the cable 30 is anchored to prevent the cable 30 from being drawn back lest the steering function be abnormal.

In the case of using the laser fusion device, the laser light is focused at one end of the cable to melt it, and the molten material agglomerates to form the cephalization structure 32. The laser fusion device can produce a high-strength and high-precision cephalization structure 32 without using an adhesive agent or auxiliary material. The laser fusion technology can lower cost and reduce pollution. Further, the laser fusion technology favors automatic fabrication, raises the fabrication efficiency and stabilizes quality.

Figure 8A:
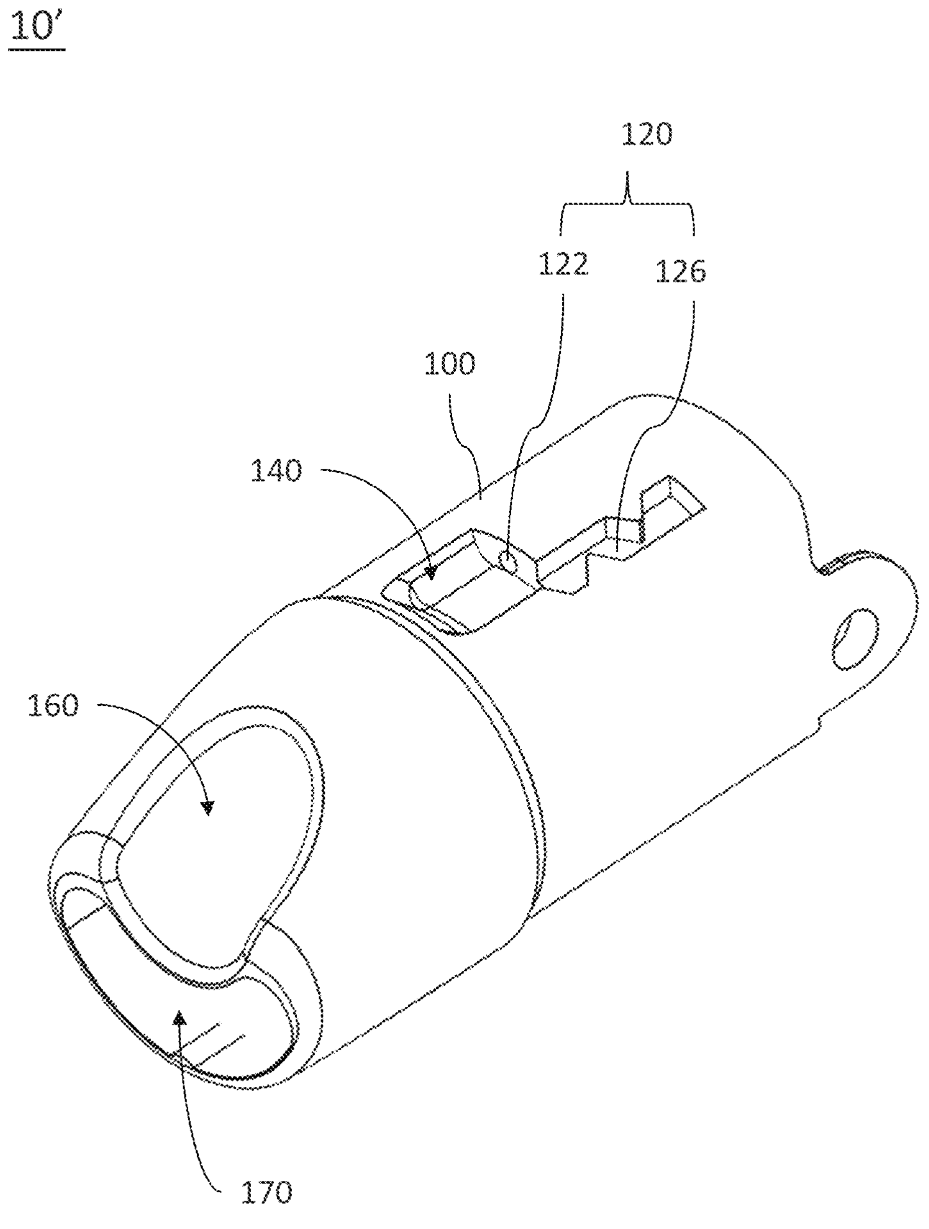
FIG. 8A is a diagram schematically showing a front-end assembly of a cable anchoring device for an endoscope according to a third embodiment of the present invention.
Figure 8B:
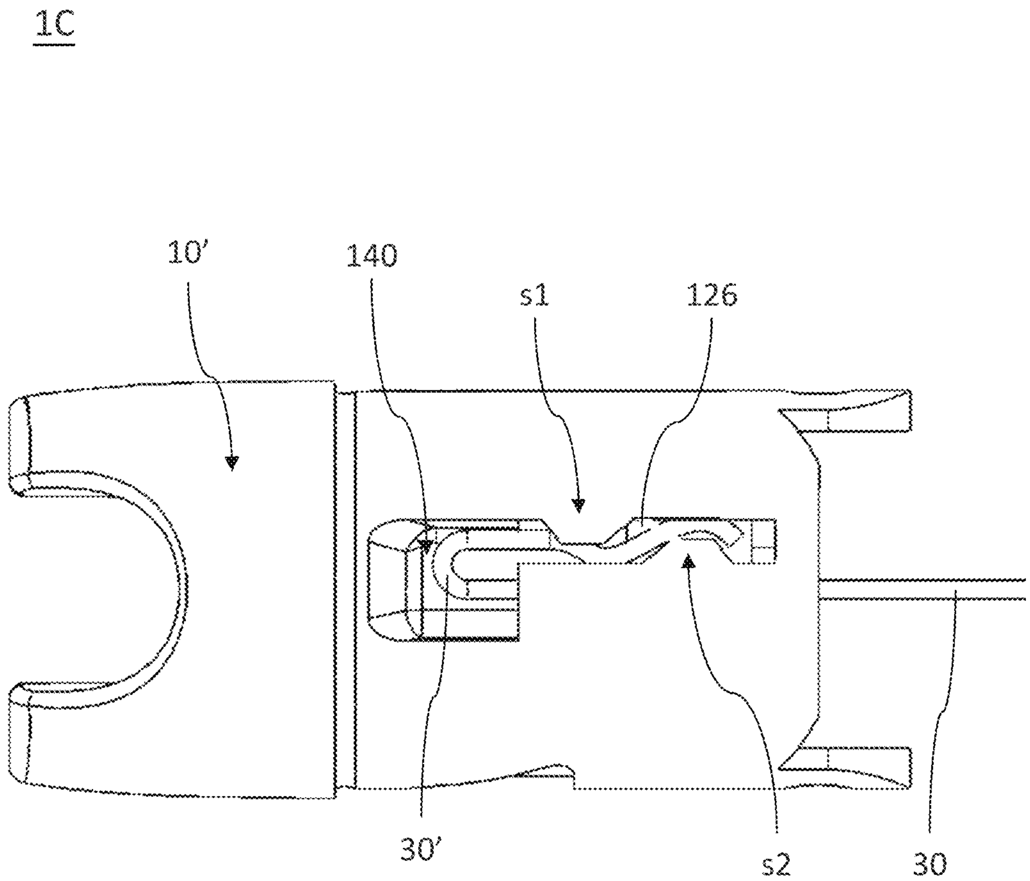
FIG. 8B is a diagram schematically showing the cable anchoring device for an endoscope according to the third embodiment of the present invention.

Below is introduced a third embodiment of the present invention. Refer to FIG. 8A and FIG. 8B. The cable anchoring device for an endoscope 1C of the third embodiment is different from that of the first embodiment in that a front-end assembly 10' of the cable anchoring device for an endoscope 1C of the third embodiment does not have the second channel. In the third embodiment, the channel part 120 includes a first channel 122 and a trench 126. The other parts of the third embodiment is the same as those of the first embodiment and will not repeat herein. The first channel 122 is located between two ends of the front-end assembly 10'. One end of the first channel 122 has a first via-hole h1, and another end of the first channel 122 has a second via-hole h2. The trench 126 is a recessed portion arranged in a region where a surface 100 of the front-end assembly 10' and the groove 140 interconnect. One end of the cable 30 may pass through the first via-hole h1, the first channel 122, the second via-hole h2 and the groove 140 in sequence and then enters the trench 126, whereby the cable 30 is constrained by the trench 126. The resin 50 may be dispensed inside the trench 126 to fix a portion of the cable 30. The open trench 126 favors inserting the cable 30 and thus saves fabrication time. Further, the guiding of the trench 126 gives a correct direction lest the cable 30 be inserted to a wrong direct. The positions where the first via-hole h1, the second via-hole h2 and the resin 50 are labelled have been introduced hereinbefore. For simplicity, those symbols are not labelled in the drawings. However, the persons having ordinary knowledge in the art should be able to learn the positions of the elements according to the first embodiment.

A first protrusion s1 may be established on one side of the trench 126, and a second protrusion s2 may be established on another side of the trench 126, wherein the first protrusion s1 and the second protrusion s2 are arranged in a staggering way. The first protrusion s1 and the second protrusion s2 are used to confine the cable 30 inside the trench 126. Thereby, the first protrusion s1 and the second protrusion s2 clamp the cable 30 to the trench 126 to prevent the cable 30 and the loop 30' from popping up. Miniaturizing the front-end assembly has become an inevitable trend. Even though the front-end assembly 10' is very tiny, the present invention can still make one end of the cable 30 fixed in the trench 126 without inserting the cable 30 and then pulling back the cable 30. Therefore, the present invention not only can prevent from incorrect insertion in fabrication but also can simplify the fabrication process to promote the overall fabrication efficiency and raise the yield.

Figure 9A:
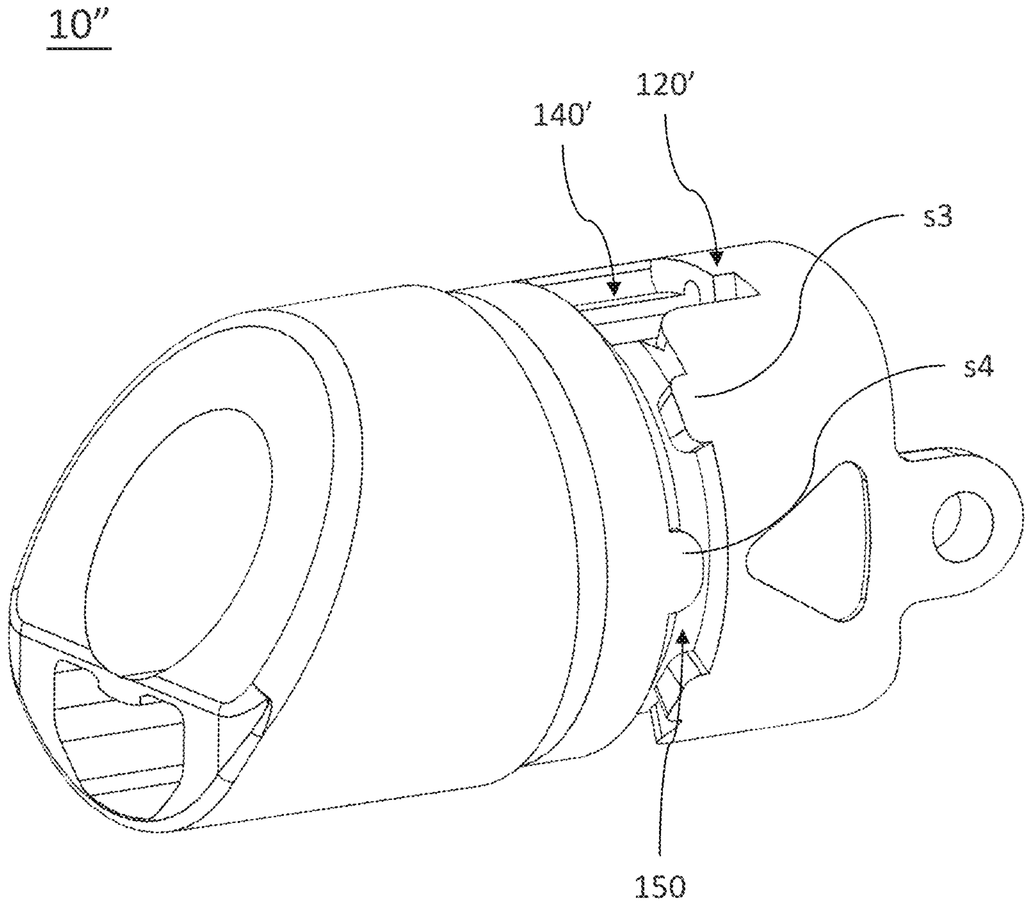
FIG. 9A is a diagram schematically showing a front-end assembly of a cable anchoring device for an endoscope according to a fourth embodiment of the present invention.
Figure 9B:
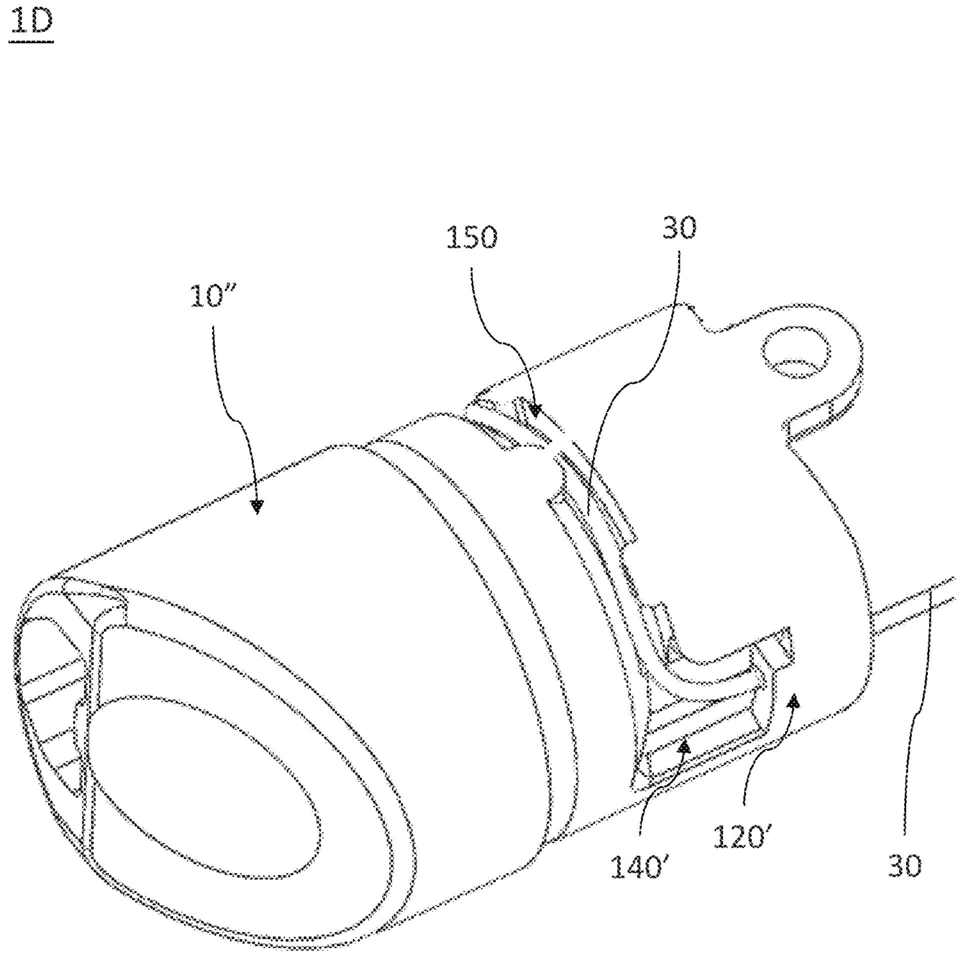
FIG. 9B is a diagram schematically showing the cable anchoring device for an endoscope according to the fourth embodiment of the present invention.

Below is introduced a fourth embodiment of the present invention. Refer to FIG. 9A and FIG. 9B. The cable anchoring device for an endoscope 1D of the fourth embodiment comprises a front-end assembly 10", a cable 30, and a resin 50. The resin 50 has been described in detail in the abovementioned embodiments. For clearness of drawings, the resin is not depicted in the drawings. The persons having ordinary knowledge in the art should be able to learn the position of the resin according to the abovementioned embodiments. The front-end assembly 10" includes channel parts 120' corresponding to two sides of the front-end assembly 10", grooves 140' corresponding to two sides of the front-end assembly 10", and an outer-rim trench 150 connected with the grooves 140' respectively at the left and right sides. Two sides of the front-end assembly 10" respectively have channel parts 120' and grooves 140'. Each of the channel parts 120', which are respectively disposed on two sides, is formed between two ends of the front-end assembly 10". Each of the grooves 140' which are respectively disposed on two sides, is formed between one end of the front-end assembly 10" and the channel part 120'. The channel parts 120', which are separately disposed on two sides, respectively interconnect with the corresponding grooves 140', which are separately disposed on two sides. The outer-rim trench 150 is extended along the outer diameter of the front-end assembly 10". Two ends of the outer-rim trench 150 interconnect with the grooves 140, which are separately disposed on two sides. Thereby, another portion of the cable 30 is received by the outer-rim trench 150 and the grooves 140' separately disposed on two sides. It should be noted: in general, an endoscope needs two cables, which are respectively arranged on two sides to facilitate steering the endoscope. However, the embodiment only needs a single cable 30. A portion of the cable 30 is inserted into the channel part 120' and the groove 140', which are on the same sides, and then inserted into the outer-rim trench 150. Next, the cable 30 runs along the outer-rim trench 150 and then is inserted into the channel part 120' and the groove 140', which are on the other sides. The resin 50 may be dispensed into the grooves 140', which are separately disposed on two sides, and the outer-rim trench 150, whereby the cable 30 is fixed and the material cost is reduced.

In the fourth embodiment, a third protrusion s3 and a fourth protrusion s4 may be formed in the outer-rim trench 150. The third protrusion s3 and the fourth protrusion s4 are respectively disposed on two sides of the outer-rim trench 150 and arranged in a staggering way. Thereby, the cable 30 is confined inside the outer-rim trench 150.

In conclusion, the cable anchoring device for an endoscope of the present invention favors steering the endoscope and applies to mechanical steering, electrical steering and magnetic steering. No matter whether the steering is driven by a hand crank, a turning knob, an electric motor, a server, or a magnetic device, the cable anchoring device for an endoscope of the present invention can guide the sensing/illuminating module to the desired direction. The present invention can expand the inspection area of the endoscope and raise the accuracy in complicated and curved channels. Further, the present invention can decrease the time and difficulty of operating an endoscope as well as increase the efficiency and safety of inspection.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the appended claims.

What is claimed is:

1. A cable anchoring device for an endoscope, comprising:

a front-end assembly, including:

a channel part, disposed between two ends of the front-end assembly; and a groove, disposed between one end of the front-end assembly and the channel part, wherein the channel part interconnects with the groove, the groove includes a bottom, a lateral face, and a guiding face opposite to the lateral face, the lateral face is adjacent to the channel part, and the guiding face extends obliquely upward from the bottom of the groove to an outer surface of the groove to form a slope;

a cable, wherein a portion of the cable is inserted into the channel part and the groove, and the portion of the cable is formed into a loop or a cephalization structure; and a resin, disposed inside the groove and used to fix the loop or the cephalization structure of the portion of the cable disposed inside the groove.

2. The cable anchoring device for endoscope according to claim 1, wherein the channel part includes:

a first channel, wherein one end of the first channel has a first via-hole, and another end of the first channel has a second via-hole; and a second channel, wherein one end of the second channel has a third via-hole, and another end of the second channel has a fourth via-hole, wherein the cable is inserted into the first channel through the first via-hole, protrudes into the groove through the second via-hole, and then is inserted into the second channel through the fourth via-hole.

3. The cable anchoring device for endoscope according to claim 2, wherein at least one of the first via-hole, the second via-hole, the third via-hole and the fourth via-hole is a trumpet-shaped opening.

4. The cable anchoring device for endoscope according to claim 1, wherein a size of the cephalization structure is larger than a diameter of an opening of the channel part.

5. The cable anchoring device for endoscope according to claim 1, wherein the channel part includes;

a first channel, wherein one end of the first channel has a first via-hole, and another end of the first channel has a second via-hole;

a trench, being a recessed portion arranged in a region where a surface of the front-end assembly and the groove interconnect, wherein one end of the cable passes through the first via-hole, the first channel, the second via-hole and the groove in sequence; then the cable is inserted into the trench and constrained by the trench.

6. The cable anchoring device for endoscope according to claim 5, wherein a first protrusion is formed on one side of the trench, and a second protrusion is formed on another side of the trench; the first protrusion and the second protrusion are arranged in a staggering way; the first protrusion and the second protrusion are used to confine the cable inside the trench.

7. The cable anchoring device for endoscope according to claim 5, wherein the resin is dispensed into the trench to fix a portion of the cable.

8. The cable anchoring device for endoscope according to claim 1, wherein the front-end assembly further includes an outer-rim trench; the outer-rim trench is extended along a diameter of the front-end assembly and interconnected with the groove; another portion of the cable is received by the outer-rim trench and the groove.

9. The cable anchoring device for endoscope according to claim 8, wherein a third protrusion and a fourth protrusion are formed in the outer-rim trench; the third protrusion and the fourth protrusion are respectively arranged on two sides of the outer-rim trench in a staggering way to confine the cable inside the outer-rim trench.

10. The cable anchoring device for endoscope according to claim 8, wherein the resin is dispensed into the outer-rim trench to fix a portion of the cable.

* * * * *